US012752084B2

(12) United States Patent
Boud et al.

(10) Patent No.: US 12,752,084 B2
(45) Date of Patent: Oct. 6, 2026

(54) INSTRUMENT DELIVERY DEVICE WITH NESTED HOUSING

(71) Applicant: Becton, Dickinson and Company, Franklin Lakes, NJ (US)

(72) Inventors: Adam J. Boud, Bluffdale, UT (US); Weston F. Harding, Lehi, UT (US); Curtis H. Blanchard, Herriman, UT (US); Megan S. Scherich, Salt Lake City, UT (US); Jonathan Karl Burkholz, Salt Lake City, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 924 days.

(21) Appl. No.: 17/901,016

(22) Filed: Sep. 1, 2022

(65) Prior Publication Data

US 2024/0075250 A1 Mar. 7, 2024

(51) Int. Cl.

*A61M 25/06* (2006.01)
*A61B 5/15* (2006.01)
*A61M 25/00* (2006.01)
*A61M 25/01* (2006.01)
*A61M 39/10* (2006.01)

(52) U.S. Cl.

CPC ... *A61M 25/0606* (2013.01); *A61B 5/150992* (2013.01); *A61M 2025/0004* (2013.01); *A61M 2025/0175* (2013.01); *A61M 2039/1077* (2013.01)

(58) Field of Classification Search

CPC ........ A61M 25/0606; A61M 25/09041; A61M 25/0113; A61M 25/0102; A61M 2025/0004; A61M 2025/0175; A61B 5/150992

See application file for complete search history.

(56) References Cited

U.S. PATENT DOCUMENTS 3,739,778 A * 6/1973 Monestere, Jr. ... A61M 25/0111 604/167.01
5,466,222 A * 11/1995 Ressemann ........... A61M 29/02 604/524

(Continued)

FOREIGN PATENT DOCUMENTS

WO 2021236530 A1 11/2021
WO 2022032242 A1 2/2022

OTHER PUBLICATIONS

Extended European Search Report issued in EP23861279.0 on Jul. 2, 2026.

*Primary Examiner* — William R Carpenter
*Assistant Examiner* — Robert F Allen
(74) *Attorney, Agent, or Firm* — The Webb Law Firm

(57) ABSTRACT

Provided herein is a medical device, including an instrument having a proximal end and a distal end, an introducer configured to moveably receive the instrument and having an outer housing having a proximal end, a distal end, and a sidewall therebetween defining an inner volume and an inner housing having a proximal end, a distal end, and a sidewall therebetween defining an inner volume, the inner housing slidably received within the outer housing, the distal end of the introducer configured to couple the introducer to an intravenous line. The inner housing is configured to move relative to the outer housing to move the instrument between a first position and a second position.

24 Claims, 11 Drawing Sheets

(56) References Cited

U.S. PATENT DOCUMENTS 9,744,344 B1 * 8/2017 Devgon ............ A61M 39/0247
11,173,277 B2 * 11/2021 Burkholz .......... A61M 25/0017
11,389,624 B2 7/2022 Cook
12,343,146 B2 7/2025 Blanchard et al.
2008/0119795 A1 * 5/2008 Erskine ............ A61M 25/0618 604/263
2010/0210934 A1 * 8/2010 Belson ............... A61B 17/3421 604/164.11
2012/0041392 A1 * 2/2012 Donawick ......... A61M 25/0612 604/267
2012/0277627 A1 * 11/2012 Devgon ........... A61B 5/150717 600/576
2012/0277630 A1 11/2012 Devgon
2013/0018359 A1 * 1/2013 Coyle ............. A61M 25/09041 604/528
2013/0199522 A1 * 8/2013 Shockley .............. A61M 16/04 128/200.26
2014/0128775 A1 * 5/2014 Andreae ................ A61B 5/153 600/581
2014/0364766 A1 * 12/2014 Devgon ........... A61B 5/150396 600/581
2017/0216564 A1 * 8/2017 Devgon ............ A61M 25/0606
2017/0224202 A1 * 8/2017 Su ...................... A61B 1/00133
2018/0207406 A1 * 7/2018 Ishida ............... A61M 25/0631
2018/0207440 A1 7/2018 Tseng
2019/0021640 A1 * 1/2019 Burkholz ......... A61B 5/150992
2019/0321590 A1 10/2019 Burkholz et al.
2019/0321595 A1 * 10/2019 Spataro ........... A61M 25/09041
2020/0016374 A1 * 1/2020 Burkholz ........... A61M 25/0113
2020/0023166 A1 * 1/2020 Burkholz ........... A61M 25/0111
2020/0046948 A1 * 2/2020 Burkholz ............... A61B 5/154
2020/0100716 A1 * 4/2020 Devgon ............. A61B 5/15003
2020/0170559 A1 * 6/2020 Burkholz ......... A61B 5/150992
2020/0230353 A1 * 7/2020 Burkholz .............. A61M 25/00
2020/0230358 A1 7/2020 Devgon et al.
2020/0316346 A1 * 10/2020 Burkholz ........ A61M 25/09041
2021/0154439 A1 * 5/2021 Blanchard ....... A61M 25/09041
2021/0186394 A1 * 6/2021 Ma ..................... A61B 5/15003
2021/0212618 A1 * 7/2021 Burkholz ......... A61B 5/150267
2021/0213268 A1 * 7/2021 Scherich ......... A61M 25/09041
2021/0228121 A1 * 7/2021 Burkholz ......... A61B 5/150221
2021/0228842 A1 * 7/2021 Scherich ............... A61M 25/09
2021/0290126 A1 * 9/2021 Burkholz ......... A61B 5/150992
2021/0290247 A1 * 9/2021 Burkholz ......... A61B 17/12145
2021/0290264 A1 * 9/2021 Harding ............ A61M 25/0097
2021/0290897 A1 * 9/2021 Burkholz .............. A61M 39/02
2021/0290901 A1 * 9/2021 Burkholz ......... A61B 5/150015
2021/0290905 A1 9/2021 Harding et al.
2021/0290906 A1 * 9/2021 Burkholz ........... A61B 5/15003
2021/0290914 A1 * 9/2021 Burkholz .............. A61M 25/09
2021/0290926 A1 * 9/2021 Scherich ........... A61M 25/0097
2021/0299426 A1 * 9/2021 Scherich .......... A61B 5/150992
2021/0393921 A1 * 12/2021 Burkholz .......... A61M 25/0017
2021/0393924 A1 * 12/2021 Burkholz .............. A61M 25/09
2021/0402152 A1 * 12/2021 Burkholz ........ A61M 25/09041
2022/0110561 A1 * 4/2022 Blanchard .......... A61B 5/15003
2022/0161003 A1 * 5/2022 Cook ................ A61M 25/0606
2022/0168547 A1 * 6/2022 Ma .................... A61M 25/0606
2022/0218252 A1 * 7/2022 Blanchard ........ A61B 5/150992
2022/0218955 A1 7/2022 Scherich et al.
2022/0218956 A1 7/2022 Harding et al.
2022/0313958 A1 * 10/2022 Harding ............ A61M 25/0606
2022/0313973 A1 * 10/2022 Blanchard ....... A61M 25/09041
2022/0379074 A1 * 12/2022 Burkholz .............. A61M 25/00
2022/0379104 A1 * 12/2022 Blanchard ....... A61M 25/09041
2023/0001159 A1 1/2023 Lackey et al.
2023/0135731 A1 * 5/2023 Farrar .............. A61B 5/150732 600/581
2023/0136086 A1 5/2023 Boud et al.
2023/0137347 A1 * 5/2023 Harding ........... A61B 5/150992 600/581
2023/0270987 A1 * 8/2023 Blanchard ......... A61M 39/0247 604/175
2024/0075252 A1 * 3/2024 Boud ................ A61M 25/0074

* cited by examiner

INSTRUMENT DELIVERY DEVICE WITH NESTED HOUSING

BACKGROUND OF THE INVENTION

Field of the Invention

The present disclosure relates generally to medical devices for use with intravenous (IV) catheters and, more specifically, to medical devices with features for improving performance in terms of accessing the vasculature.

Description of Related Art

Instrument delivery devices, including those used for collecting blood, when used with indwelling IV catheters can include displaceable implements that are advanced beyond the tip of the indwelling catheter. Often, when the displaceable implement is advanced, it can encounter an obstruction, resulting in deflection of the implement. Examples of obstructions include the friction of the seal within the delivery device, torturous path within an integrated catheter, pinching of the catheter tubing as it dives into the skin, thrombus, fibrin, and valves. Further, delivery of instruments can be complicated by interchange of instruments, and the necessary length for deployment of such instruments. Accordingly, a need exists in the art for instrument delivery devices that allow for robust performance of the instrument that is being delivered.

SUMMARY OF THE INVENTION

Provided herein is a medical device, including an instrument having a proximal end and a distal end, an introducer configured to moveably receive the instrument and having an outer housing having a proximal end, a distal end, and a sidewall therebetween defining an inner volume, and an inner housing having a proximal end, a distal end, and a sidewall therebetween defining an inner volume, the inner housing slidably received within the outer housing, the distal end of the introducer configured to couple the introducer to an intravenous line, and wherein the inner housing is configured to move relative to the outer housing to move the instrument between a first position, in which the instrument is disposed within the outer housing, and a second position, in which the distal end of the instrument is disposed beyond the distal end of the outer housing such that at least a first portion of the instrument is disposed within the intravenous line when the introducer is coupled to the intravenous line.

Also provided herein is a system including a catheter assembly including a catheter adapter having a distal end, a proximal end, a lumen extending between the distal end and the proximal end, and a side port arranged between the distal end and the proximal end, the side port in fluid communication with the lumen, a catheter secured to the distal end of the catheter adapter and extending distally from the catheter adapter, a fluid conduit having a proximal end coupled to the side port and a distal end, the fluid conduit in fluid communication with the side port, and a medical device as described herein.

DESCRIPTION OF THE INVENTION

Figure 1A:
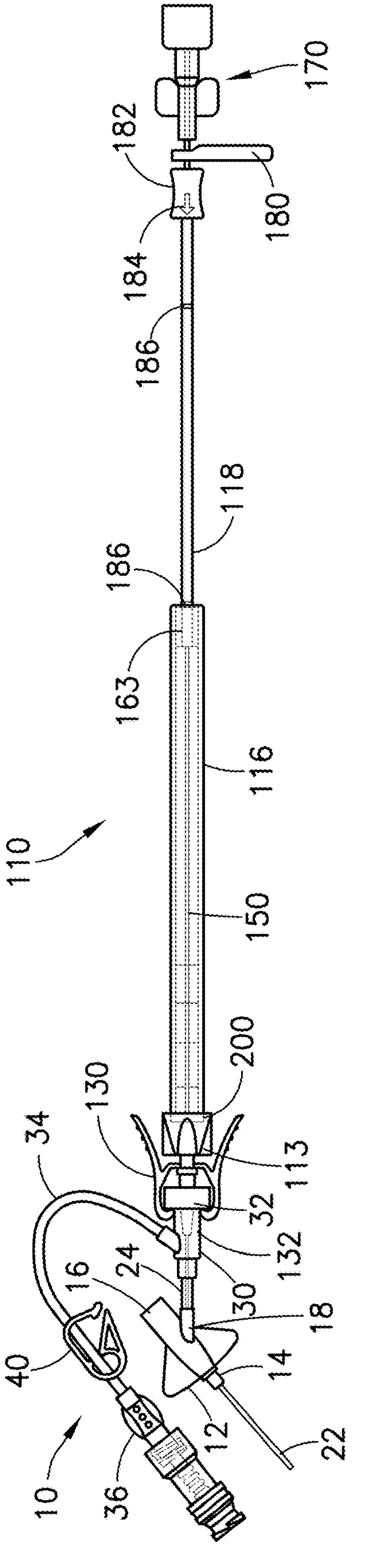
FIGS. 1A-1B are top views of a medical device according to non-limiting embodiments described herein.

The following description is provided to enable those skilled in the art to make and use the described embodiments contemplated for carrying out the invention. Various modifications, equivalents, variations, and alternatives, however, will remain readily apparent to those skilled in the art. Any and all such modifications, equivalents, variations, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

It should be understood that any numerical range recited herein is intended to include all values and sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value equal to or less than 10.

Provided herein are devices and systems for delivering instruments through indwelling catheters, such as peripheral intravenous catheters (PIVCs). While certain devices (e.g., blood draw devices) are discussed below in terms of devices that may be used with PIVCs, and exemplified in the attached drawings, those of skill will appreciate that any number of different devices for introducing an instrument, including instruments ranging from tubes, probes, sensors (e.g., pressure sensors, pH sensors, lactate sensors, glucose sensors, and the like), wiring, fiber optics, guidewires, etc., may be used within the scope of the present disclosure.

Figure 1B:
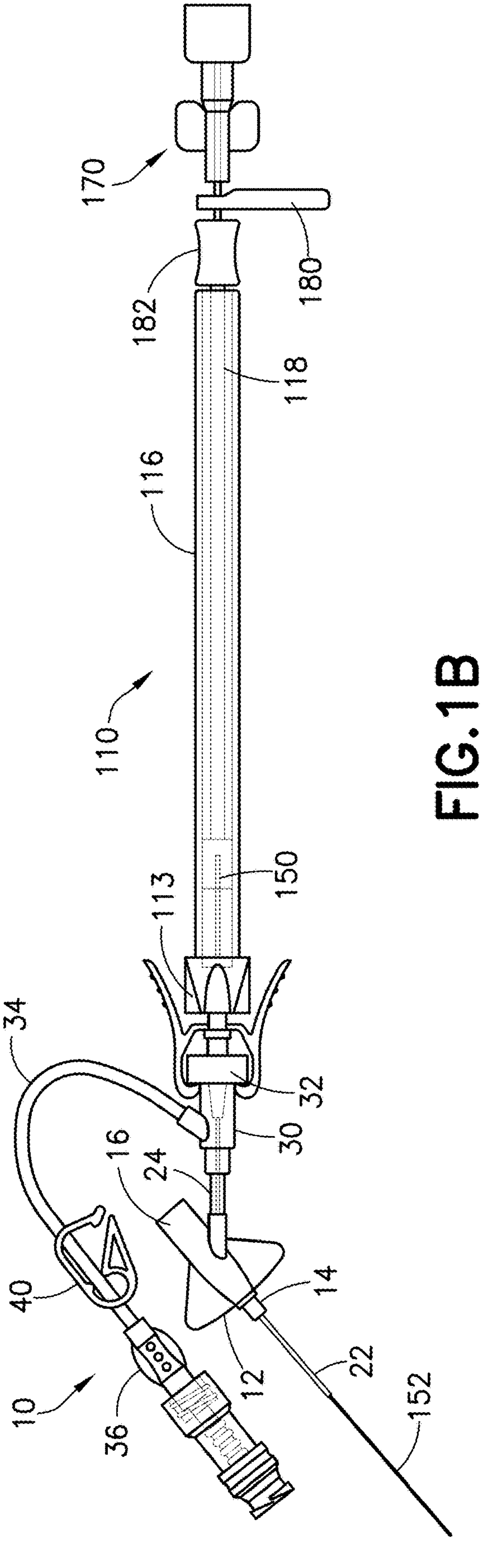

Referring now to FIGS. 1A and 1B, shown is a non-limiting embodiment of a system including a catheter assembly 10 and instrument delivery device 110. Suitable catheter assemblies for use with instrument delivery devices described herein are commercially available, for example from Becton, Dickinson and Company under the trade name NEXIVA. Cather assembly 10 may include a catheter adapter 12, which may include a distal end 14 and a proximal end 16. In some embodiments, the catheter adapter 12 may include one or more additional ports 18. In some embodiments, port 18 may be disposed between the distal end 14 and the proximal end 16. In some embodiments, more than one port 18 may be disposed between the distal end 14 and the proximal end 16. In some embodiments, port 18 may be disposed at proximal end 16. In some embodiments, the first catheter adapter 12 may include a first lumen (not shown) extending through the distal end 14 and the proximal end 16. First lumen may be sealed at proximal end 16 of catheter adapter 12.

In some non-limiting embodiments or aspects, the catheter assembly 10 may include a catheter 22 extending from the distal end 14. In some embodiments, the first catheter 22 may include a peripheral intravenous catheter, a midline catheter, or a peripherally-inserted central catheter. Catheter 22 may be formed of any suitable material and may be of any useful length, as known to those of skill in the art. In some non-limiting embodiments or aspects, the catheter assembly 10 may include a first fluid conduit 24 extending from the port 18. First fluid conduit 24 may be formed of any suitable material known to those of skill in the art, and may have a distal end and a proximal end, and first fluid conduit 24 may be coupled, at distal end thereof, to port 18. In some non-limiting embodiments or aspects, a connector 30 may be coupled to a proximal end of first fluid conduit 24. Connector 30 may be a t-connector (e.g., one side port arranged at a 90 degree angle relative to a longitudinal axis of connector 30), a y-connector (e.g., one side port arranged between a 15 and a 165 degree angle relative to a longitudinal axis of connector 30), or any other type of connector known in the art, and may include a second lumen therethrough, having any number of branches suitable for the type of connector.

In some non-limiting embodiments or aspects, catheter assembly 10 may include an extension set (integrated into or removably coupleable to catheter adapter 12, connector 30, and/or needleless access connector 32) including a second fluid conduit, such as second fluid conduit 34. Extension sets are known to those of skill in the art and are commercially available from, for example, Becton, Dickinson and Company. In some non-limiting embodiments or aspects, second fluid conduit 34 may include a luer connection 36 at an end thereof. In some non-limiting embodiments or aspects, the extension set may include a clamp 40, to allow for occlusion of second fluid conduit 34. Clamp 40 and second fluid conduit 34 may be formed of any suitable materials known to those of skill in the art. In non-limiting embodiments, second lumen (e.g., within connector 30) has an inner diameter that is substantially equivalent to an inner diameter of first fluid conduit 24 and/or second fluid conduit 34.

Catheter assembly 10 may include a needleless access connector 32 and/or a second fluid conduit 34. Suitable needleless access connectors 32 can include any split-septum connector and/or those with direct fluid path access. Needleless access connectors 32 are known to those of skill in the art and are commercially available from, for example, Becton, Dickinson and Company under the trade names Q-SYTE, and SMARTSITE. While the non-limiting embodiments of FIGS. 1A and 1B show needleless access connectors arranged at connector 30, those of skill in the art will appreciate that suitable needleless access connectors may also be arranged at luer 36. In non-limiting embodiments, needleless access connector 32 includes a septum (not shown), such as a self-healing septum. In non-limiting embodiments, the septum is a slit-type septum. As will be described below, instrument delivery device 110 may be reversibly coupleable to the needleless access connector 32, and one or more portions of the instrument delivery device may pierce the septum and access the patient's vasculature through catheter 22.

With continuing reference to FIGS. 1A and 1B, instrument delivery device 110 includes an outer housing 116 having a proximal end and a distal end, and an inner housing 118 slidably received within outer housing 116. In non-limiting embodiments, inner housing 118 and outer housing 116 are in a telescoping relationship, such that inner housing 118 may be slidably received entirely, or almost entirely, within outer housing 116. Inner housing 118 also includes a proximal end and a distal end and, in non-limiting embodiments, inner housing may have a variable diameter along its length, for example where a distal end of inner housing 118 is of a larger diameter than other portions of inner housing 118. Instrument delivery device 110 further includes an instrument, exemplified in the drawings as catheter or fluid conduit 150 having a proximal end and a distal end 152, but, as described previously and as will be appreciated by those of skill in the art, may be any medical instrument that can be delivered through catheter assembly 10 to a patient's vasculature. Fluid conduit 150 is slidably received within outer housing 116, and may be advanced and/or retracted relative to outer housing 116 by displacement of inner housing 118 relative to outer housing 116. In non-limiting embodiments, fluid conduit 150 may be advanced from a first position, in which distal end 152 of fluid conduit 150 is within instrument delivery device 110, for example within outer housing 116 and/or lock 130, and a second position, in which a distal end 152 of fluid conduit 150 is positioned distally of lock 130 and, in embodiments in which instrument delivery device 110 is coupled to catheter assembly 10, optionally distally of catheter 22. While lock 130 is exemplified as a proboscis 132 and arms in FIGS. 1A and 1B, those of skill will appreciate that any type of suitable connection may be used to secure instrument delivery device 110 to an indwelling catheter, such as catheter assembly 10, including luer connections, clips, blunt plastic cannulae, blunt metal cannulae, hybrid luers (e.g., with a cannula) friction fits, and the like.

Instruments useful with the instrument delivery device 110 described herein may be formed of any useful material. In non-limiting embodiments, instrument is a fluid conduit, which is formed of a polymer, such a polyimide-containing material, nylon, polyurethane, and other suitable polymeric materials. In addition, inner housing 118 may be formed of any suitable material, including polyethylene, polypropylene, nylon, polyurethane, and the like. Those of skill will appreciate that various materials may be suitable, so long as they minimize potential buckling of the inner housing 118. In non-limiting embodiments, inner housing 118 is formed of a material that provides resistance to buckling, such as polyethylene, polypropylene, nylon, polyurethane, and the like.

As can be appreciated, FIG. 1A shows instrument delivery device in a first state, where instrument (here, fluid conduit 150) in a first position, received within outer housing 116, and inner housing 118 is in a first position, extending proximally from outer housing. In non-limiting embodiments, inner housing 118 is coupled to or otherwise interacts with fluid conduit 150, such that as inner housing 118 is advanced distally to a second position, for example by way of a user grasping grip 182 and applying a distally-directed force to inner housing 118, fluid conduit 150 is moved to a second position, where a distal end 152 of fluid conduit 150 extends beyond outer housing 116, lock 130 (if present), and/or catheter 22. Grip 182 may be arranged at a proximal end of inner housing 118, may be overmolded over inner housing 118 and/or secured thereto by, e.g., an adhesive, and may be arranged at or near a clamp 180 suitable for occluding fluid flow through inner housing 118 and/or fluid conduit 150, as will be described in greater detail below. Grip 182 may be formed of an ergonomic material, to provide comfort while a user grips the instrument delivery device 110, and may include features to, for example, increase grip and prevent slippage while inner housing 118 is being advanced/retracted. Clamp 180 may be a slide clamp, for example as shown in FIGS. 1A and 1B, or may be a pinch clamp.

As described above, a distal end of inner housing 118 may be of a larger diameter than other portions of inner housing 118, such that, as inner housing 118 is retracted, one or more features on outer housing 116 may interact with the enlarged portion of inner housing 118 to prevent pulling inner housing 118 completely out of outer housing 116. Enlarged distal portion of inner housing 118 may include vents for allowing air to pass therethrough, reducing force needed to advance/retract inner housing 118, and, as described below, lubricant may be applied to an enlarged portion of inner housing 118 to reduce friction between inner housing 118 and outer housing 116.

Figure 2:
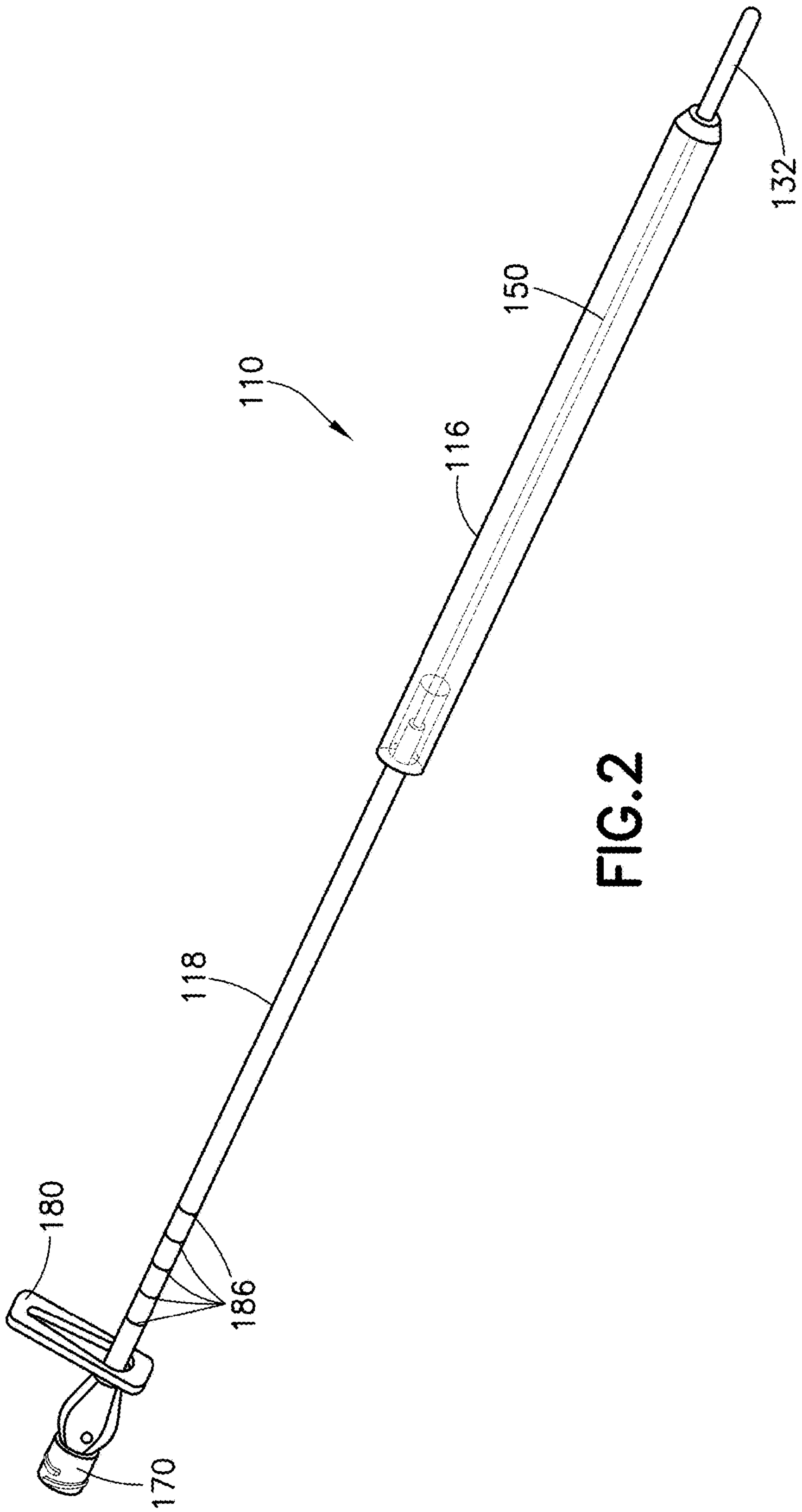
FIG. 2 is a perspective view of a medical device according to non-limiting embodiments described herein.
Figure 3:
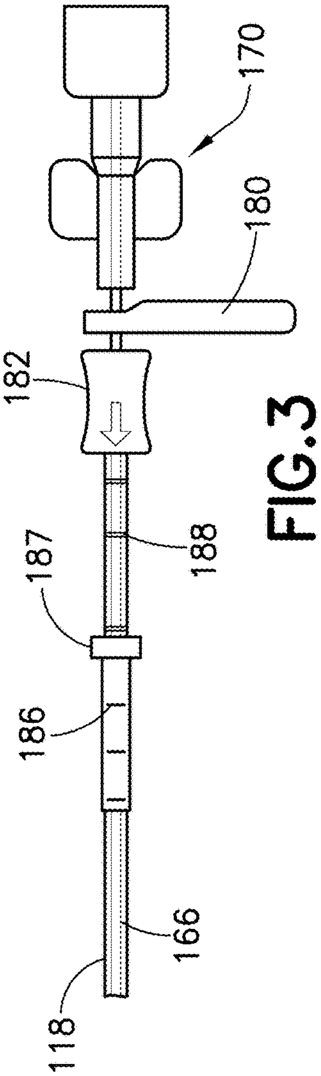
FIG. 3 is a partial side view of a medical device according to non-limiting embodiments described herein.

As will be described below, and as shown in the accompanying drawings, instrument delivery device 110 may include any number of features to provide a more robust system for accessing a patient's vasculature. With continuing reference to FIGS. 1A and 1B, as well as FIGS. 2-3, in non-limiting embodiments a joint 113 is included at distal end of outer housing 116, for example between outer housing 116 and lock 130. Suitable joints 113 may include pivoting joints, ball joints, pin joints, cylindrical joints, hinge joints, and rotating joints. Such joints 113 may increase the usability of instrument delivery device 110, for example by allowing for greater access in terms of distance from the patient's skin, as well as securement of the indwelling catheter by avoiding excessive manipulation of the catheter assembly 10 during instrument delivery and medical procedures associated therewith. In non-limiting embodiments, proboscis 132 is formed of a flexible material to allow similar pivoting and or rotational freedom to avoid excessive manipulation of the catheter assembly 10. In non-limiting embodiments, for example as shown in FIG. 4, proboscis 132 is formed of a flexible material and is arranged at distal end of outer housing 116.

Inner housing 118 may include, at a proximal end thereof, a connector 170, to allow for various medical devices to be attached to inner housing 118, for example to provide an instrument that is to be advanced into the patient's vasculature, to inject a composition into the vasculature, and/or to receive fluid withdrawn from the vasculature. Suitable connectors 170 include luer connectors, luer lock access devices, needleless access connectors, and the like known to those of skill in the art.

With continuing reference to FIG. 1A, as well as FIGS. 2-5, in non-limiting embodiments outer housing 116, inner housing 118, and/or instrument may include one or more indicia 184, 186, 191, 192 arranged on an outer or inner surface thereof, and/or embedded in the material of any component. Suitable indicia may be visual and/or tactile, and may be provided to, for example, indicate direction of advancement (e.g., indicia 184), instrument length, and/or instrument positioning relative to indwelling catheter. In non-limiting embodiments, one or more indicia 186 may be provided on inner housing 118, and outer housing 116 may be formed of a material that is at least partially transparent, to allow for visualization of indicia 186 throughout the transition from a first position of inner housing 118 to a second position of outer housing 116. In non-limiting embodiments, a separate indicia, in the form of a tactile stop 187, may be included at one or more locations along inner housing 118, to provide a user with a tactile indication of certain thresholds. For example, a tactile stop 187 may indicate that instrument (e.g., fluid conduit 150) has nearly reached its full extension and/or may indicate that the instrument can be extended no further (for example, as shown in FIG. 1B). In non-limiting embodiments, stop 187 is slidable, to account for instruments of differing lengths and/or different procedures.

Figure 4:
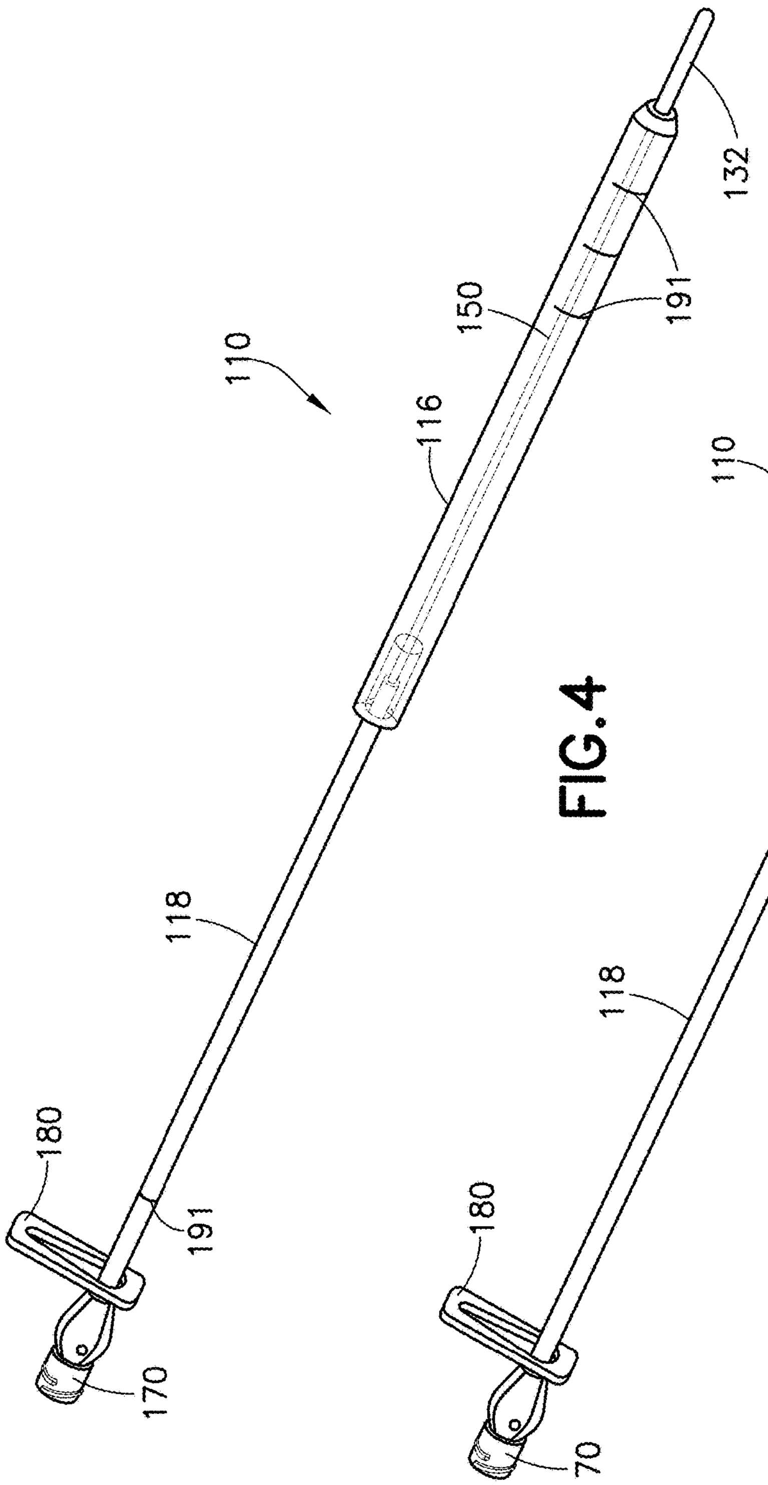
FIG. 4 is a perspective view of a medical device according to non-limiting embodiments described herein.
Figure 5:
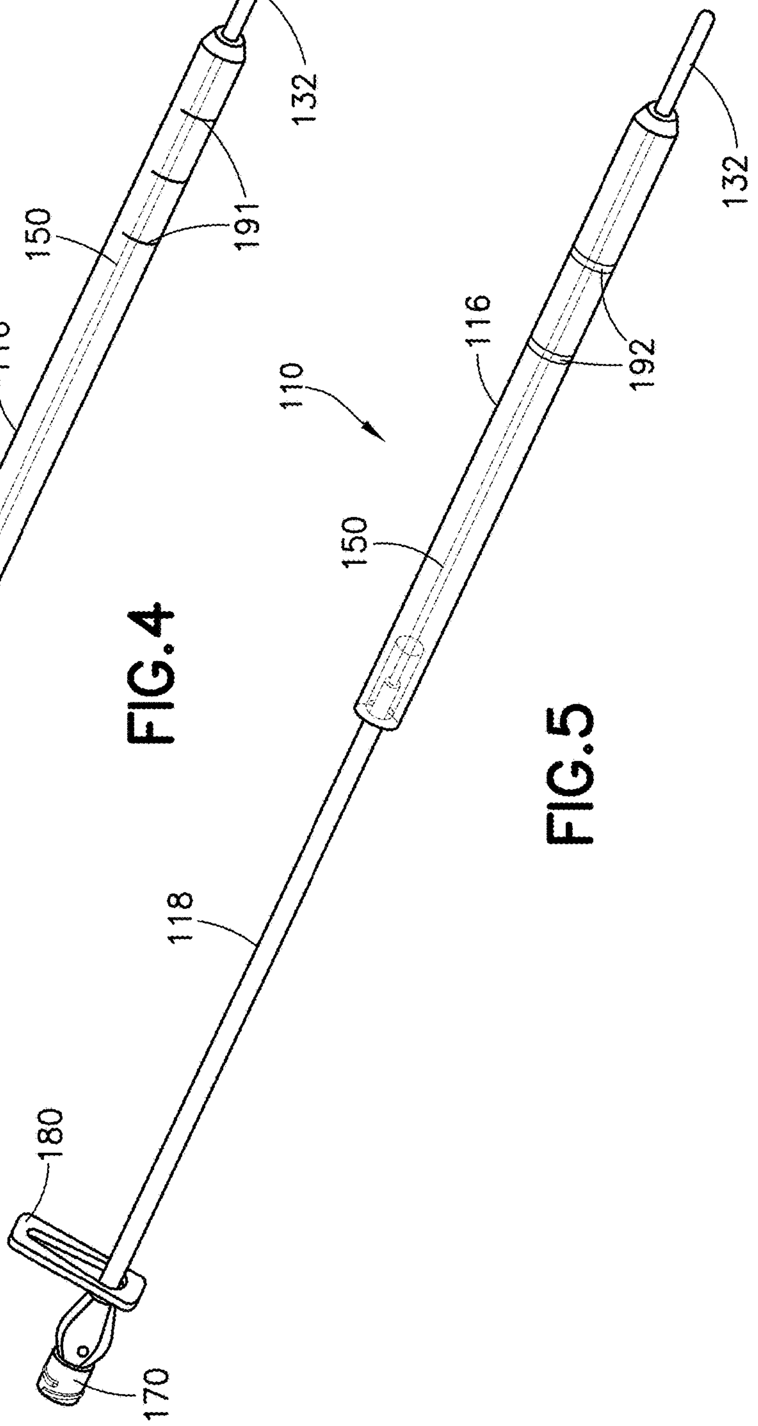
FIG. 5 is a perspective view a medical device according to non-limiting embodiments described herein.

With continuing reference to FIGS. 2-5, in non-limiting embodiments, inner housing 118 may include one or more instrument (e.g., fluid conduit 150) length indicia 188 arranged on a surface of or embedded in the material of the instrument, one or more positioning indicia 186 arranged on or embedded within material of inner housing 118, and/or a stop 187. Positioning indicia 186 may indicate position(s) of instrument relative to tip of catheter 22. In non-limiting embodiments, for example as shown in FIG. 4, inner housing 118 and outer housing 116 may include one or more corresponding pairs of depth indicia 191. In non-limiting embodiments, outer housing 116 may be substantially transparent, such that a user can align inner housing 118 and/or instrument with one or more of the depth indicia 191 arranged on outer housing 116. As shown in FIG. 5, outer housing 116 may include one or more indicia indicating when instrument is inside of catheter adapter 12, at a tip of catheter 22, and/or extending beyond the tip of catheter 22. As noted, outer housing 116 may be substantially transparent, to aid in visualization.

With continuing reference to FIGS. 1A-1B, in non-limiting embodiments a lubricant may be applied at one or more locations on or within one or more components of instrument delivery device 110. For example, a lubricant may be applied to an outer surface of a distal portion (e.g., proboscis 132) of outer housing of instrument delivery device 110 that is inserted into indwelling catheter, such as catheter assembly 10, to decrease the force necessary to couple the devices together. A lubricant may be applied at one or more locations within outer housing 116, for example on one or more outer surfaces of inner housing 118, one or more outer surfaces of instrument (e.g., fluid conduit 150). In non-limiting embodiments, one or more septa 200 may be arranged within outer housing 116, and a portion of instrument (e.g. fluid conduit 150) may be configured to pass therethrough. Lubricant may also, or alternatively, be provided about an opening through septa 200 through which instrument (e.g., fluid conduit 150) may pass. Suitable lubricants are known to those of skill in the art, and may include silicone-based lubricants. One or more septa 200 may include air venting features to allow for ease of advancement and withdrawal of instrument (e.g., fluid conduit 150). In non-limiting embodiments, proboscis 132 is configured to provide a fluid-tight seal with catheter assembly, for example by having a diameter that is closely matched to a diameter of catheter adapter 12 and/or needleless access connector 32, thereby limiting the ability of fluid to escape between an outer wall of proboscis 132 and an inner wall of catheter adapter 12 and/or needleless access connector 32. Addition of a lubricant on the proboscis can ease introduction of instrument delivery device 110 to catheter assembly 10, despite the closeness of the respective diameters.

With reference to FIG. 1A, in non-limiting embodiments, instrument delivery device 110 includes one or more supports arranged within outer housing 116, to limit and/or prevent buckling of inner housing 118 and/or instrument (e.g., fluid conduit 150) as inner housing 118 and/or the instrument (e.g., fluid conduit 150) are advanced distally through outer housing 116. Supports may include narrowed portions of outer housing 116, one or more washers arranged about inner housing 118 and/or instrument, and/or the like, for example to reduce the effective buckling length and/or buckling mode shape of inner housing 118 and/or instrument. Suitable supports are also described in U.S. Provisional Patent Application No. 63/273,226, filed Oct. 29, 2021, the contents of which are incorporated herein by reference in their entirety.

With reference to FIGS. 1A and 1B, in non-limiting embodiments, for example where instrument is a fluid conduit 150, fluid, such as blood, may be transferred into or from the patient's vasculature in which a catheter, such as catheter 22, may be indwelling. In non-limiting embodiments such as shown in FIGS. 1A and 1B, fluid conduit 150 may be joined at junction 163 to a separate fluid tube 166 that passes through inner housing 118. Separate fluid tube 166 may extend beyond a proximal end of inner housing 118, and may be coupled to connector 170, optionally through an adapter (not shown). In non-limiting embodiments, fluid conduit 150 is of a sufficient length such that it passes through inner housing 118 to couple with connector 170, optionally through an adapter. In non-limiting embodiments, inner housing 118 itself forms a fluid conduit, in fluid communication with fluid conduit 150. A separate fluid tube may be provided at proximal end of inner housing 118, and may fluidly couple inner housing 118 and connector 170, optionally through an adapter. In any of the described embodiments, an adapter may be provided to fluidly couple fluid tube 166, inner housing 118, and/or fluid conduit 150 to a connector 170, such as those described herein above.

Turning to FIGS. 6A-8B, in non-limiting embodiments, various features may be supplied to outer housing 116 and/or inner housing 118 to secure inner housing 118 and/or instrument (e.g., fluid conduit 150), in place relative to outer housing 116. In the non-limiting embodiment of FIGS. 6A-6B, outer housing 116 may include one or more first regions having a first diameter and one or more second regions having a second diameter, where the second diameter is smaller than the first diameter. A diameter of inner housing 118 may be configured to substantially match the diameter of outer housing 116 in these one or more second regions, such that friction is present as inner housing 118 engages outer housing 116 in those regions. Such friction can serve as indicia as well as a hold, securing inner housing 118 and/or instrument in place at a given insertion depth and/or advancement. With reference to FIG. 6B, in non-limiting embodiments, outer housing 116 may be tapered from a first, larger diameter at proximal end thereof to a second, smaller diameter at distal end thereof, such that as the diameter of outer housing 116 is reduced, friction between inner housing 118 and outer housing 116 increases, which may serve as indicia as well as a hold, securing inner housings 118 and/or instrument in place at a given insertion depth and/or advancement, and/or preventing too great of advancement of inner housing 118 and/or instrument.

Figure 6A:
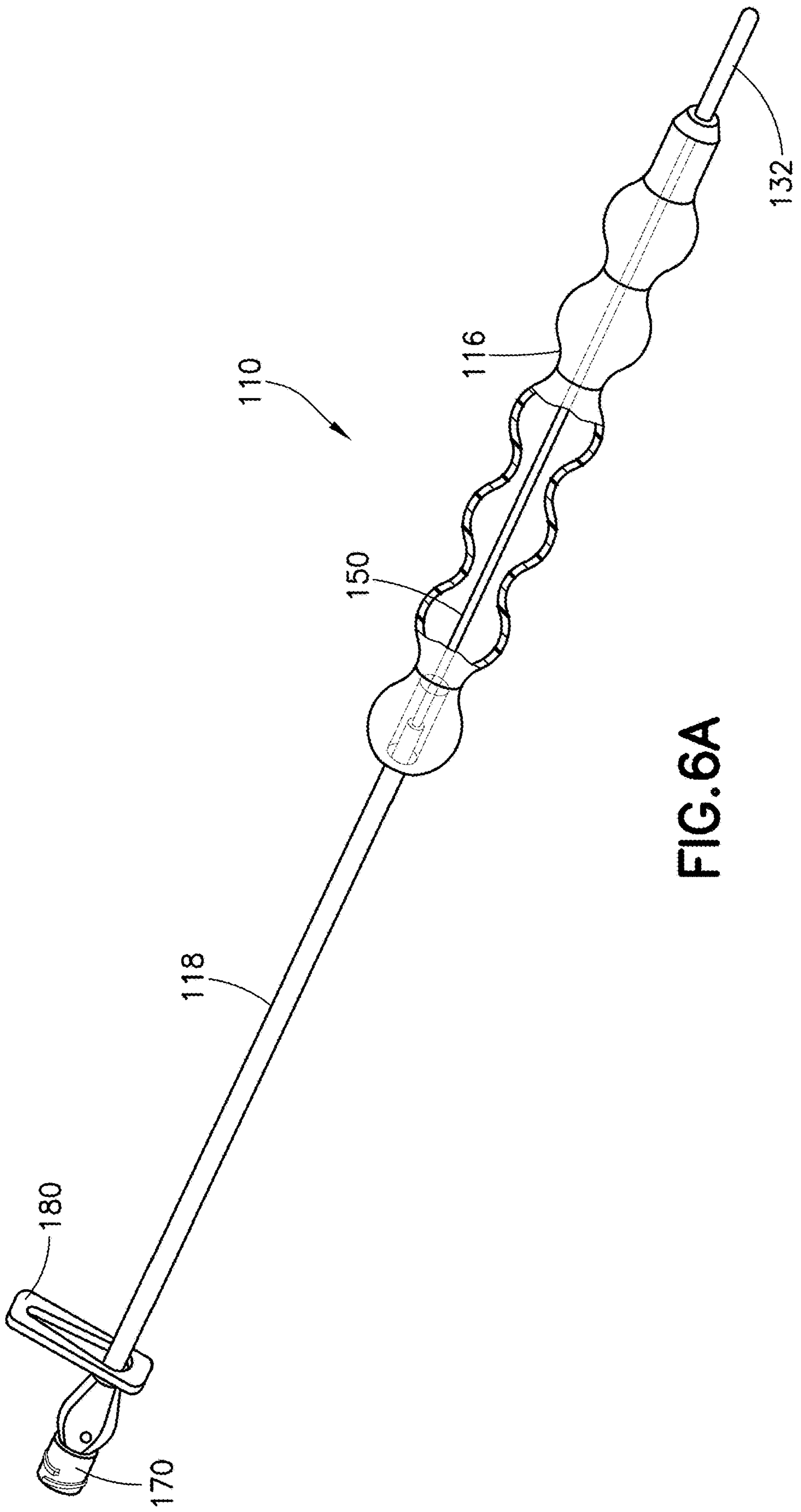
FIGS. 6A-6D are perspective and cross-sectional views of a medical device according to non-limiting embodiments described herein.
Figure 6B:
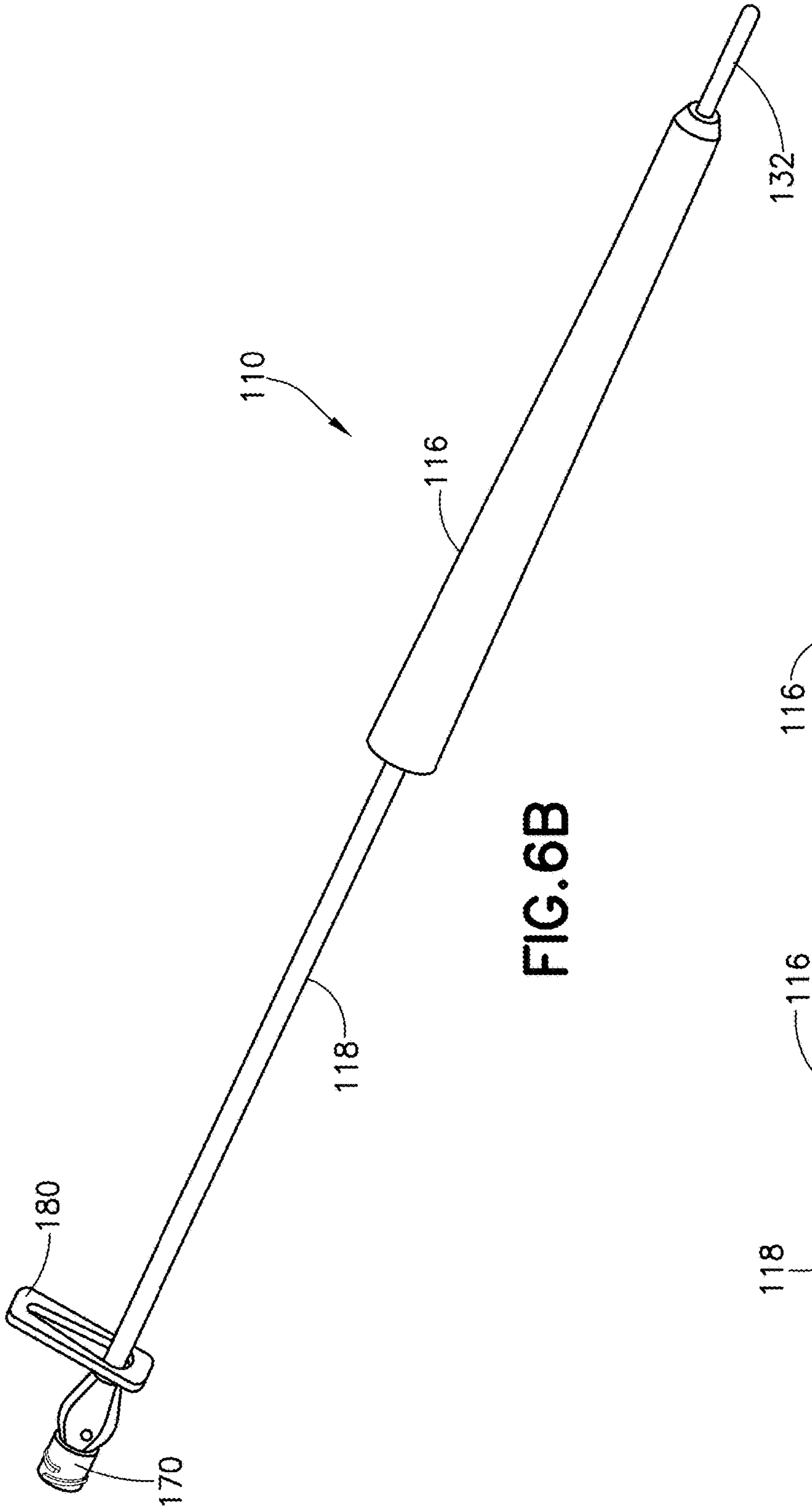
Figure 6C:
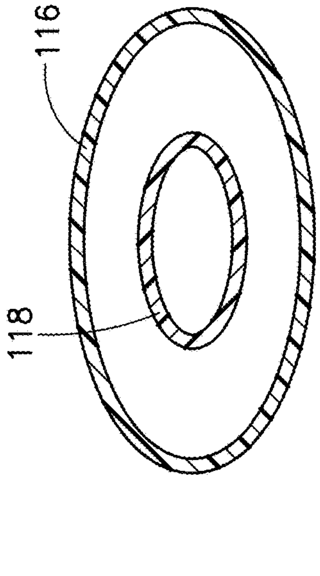
Figure 6D:
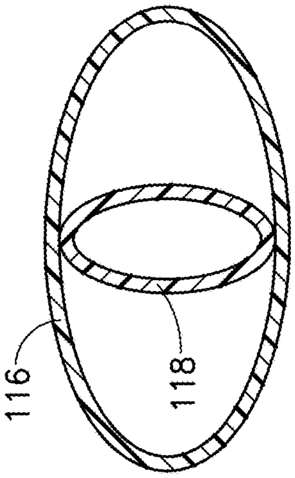
Figure 7:
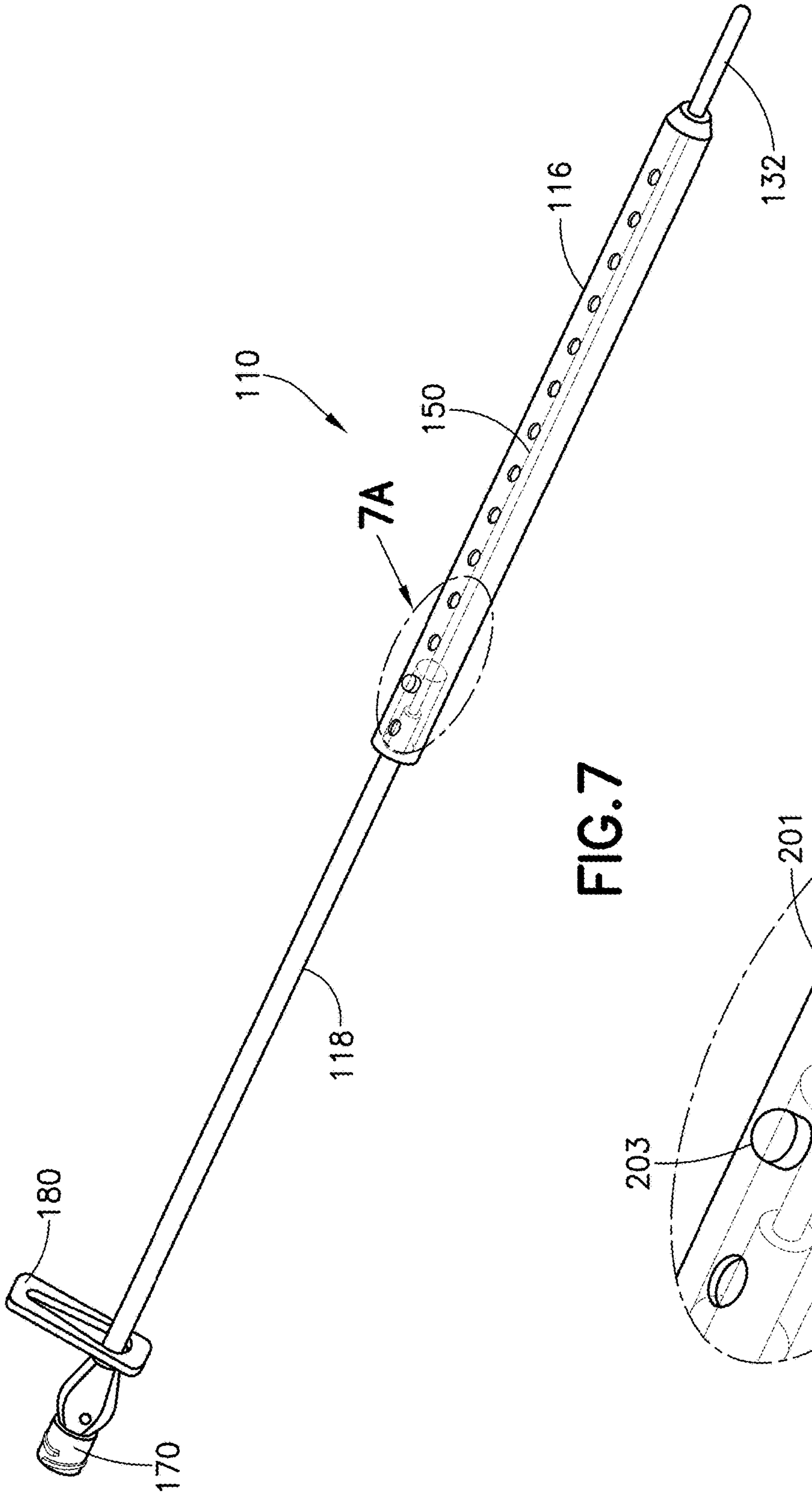
FIGS. 7-7A are perspective views of a medical device according to non-limiting embodiments described herein.
Figure 7A:
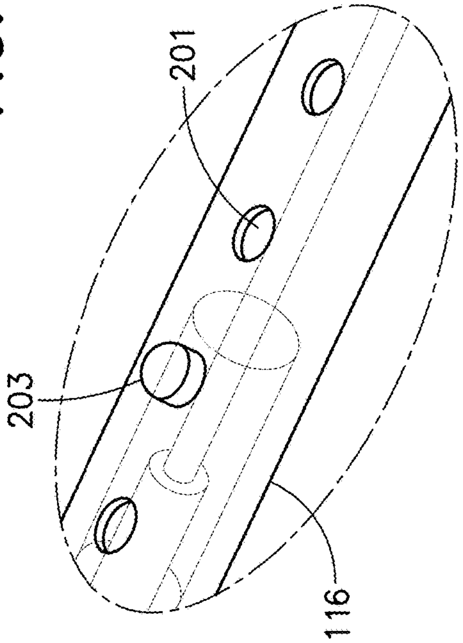

With regard to FIGS. 6C-6D, outer housing 116 and inner housing 118 may be configured to be rotatable relative to one another, and may have cross-sectional shapes, such as elliptical shapes and shown in the figures. By rotating inner housing 118 from a first, in phase configuration (FIG. 6C) to a second, out of phase configuration (FIG. 6D). By doing so, inner housing 118 may be engaged with outer housing 116, securing inner housing 118 and/or instrument in place at a given insertion depth and/or advancement.

Turning to FIGS. 7A-8B, in non-limiting embodiments locking mechanisms may be included with outer housing 116 and/or inner housing 118 to secure inner housing 118 and/or instrument in place at a given insertion depth and/or advancement. With regard to FIGS. 7-7A, in non-limiting embodiments outer housing 116 may include one or more openings therein, configured to receive one or more protrusions 203 extending radially outward from inner housing 118. One or more protrusions 203 may be biased radially outward, such that they are biased to engage one or more openings 201 in outer housing 116 and lock inner housing 118 and/or instrument in place at a given insertion depth and/or advancement. In non-limiting embodiments, one or more protrusions 203 may be spring biased, and, by pressing downward (e.g., radially inward) and/or by rotating inner housing 118, a user may disengage one or more protrusions 203 from one or more openings 201, and allow displacement of inner housing 118 and/or instrument.

Figure 8:
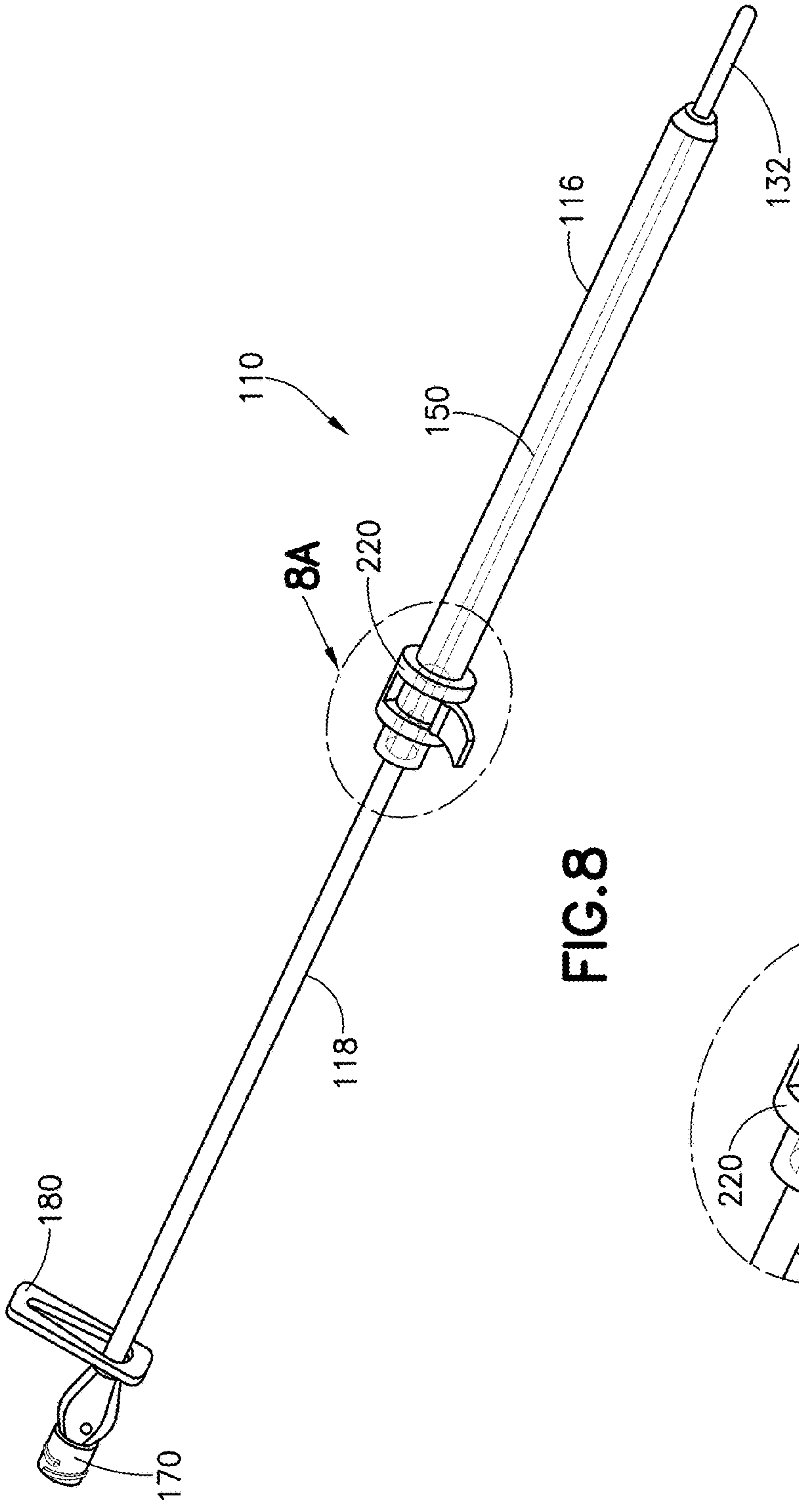
FIGS. 8-8A are perspective views of a medical device according to non-limiting embodiments described herein.
Figure 8A:
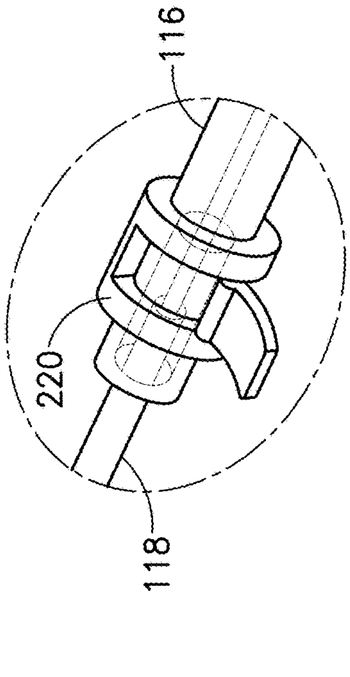

With regard to FIGS. 8-8A, in non-limiting embodiments, outer housing 116 may include one or more collars or clamps 220 at proximal end thereof. Collars and/or clamps 220 may be rotatable from a first configuration, where inner housing 118 is freely slidable relative to outer housing 116, to a second (or second, third, etc.) position where inner housing 118 is not slidable, or where ease of sliding inner housing 118 is reduced, for example to lock inner housing 118 and/or instrument in place at a given insertion depth and/or advancement. Suitable arrangements for collar and/or clamp 220 may include rotatable locking handles, threaded collars (e.g., Tuohy Borst collars), and/or any other arrangement where an effective diameter is decreased, securing and, optionally, axially compressing inner housing 118. In non-limiting embodiments, to accommodate various locking arrangements, outer housing 116 and/or inner housing 118 include one or more grips (as will be described below), venting mechanisms, and/or stress-relief elements.

Figure 9A:
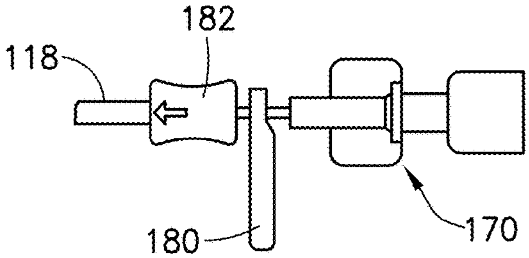
FIGS. 9A-9B are partial top views of a medical device according to non-limiting embodiments described herein.
Figure 9B:
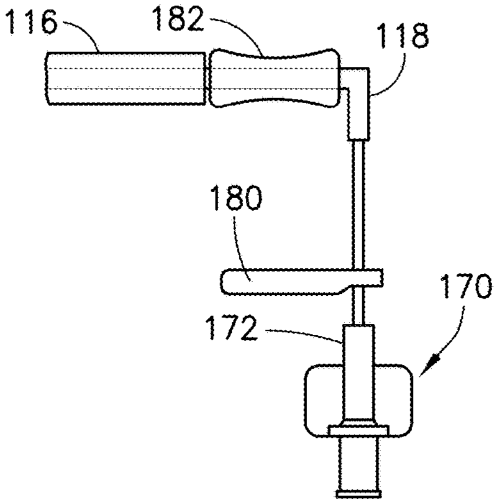

Turning to FIGS. 9A-9B, further to the connector 170 discussed above, various non-limiting arrangements of a connector 170 are shown. As shown in FIG. 9A, connector 170 may be coupled to a fluid conduit (e.g., fluid conduit 150 or 166), with a clamp 180 and grip 182 arranged distally of connector 170. Connector 170 may, as described above, be luer connectors, luer lock access devices, needleless access connectors, and the like known to those of skill in the art. As shown in FIG. 9B, outer housing 116 may include an angled portion, for example at a proximal end thereof, such that connector 170 is arranged non-parallel to a longitudinal axis of outer housing 116. In any embodiment, connector may be coupled to inner housing 118 and/or fluid conduits (e.g., fluid conduits 150 or 166) through adapter 172.

With further reference to the above, in non-limiting embodiments, inner and outer housings 118 and 116 may be configured, together with clamp 180, to provide for blood withdrawal through fluid conduit 150, when fluid conduit is in a second position (a distal end 152 thereof positioned within a patient's vasculature).

Figure 10A:
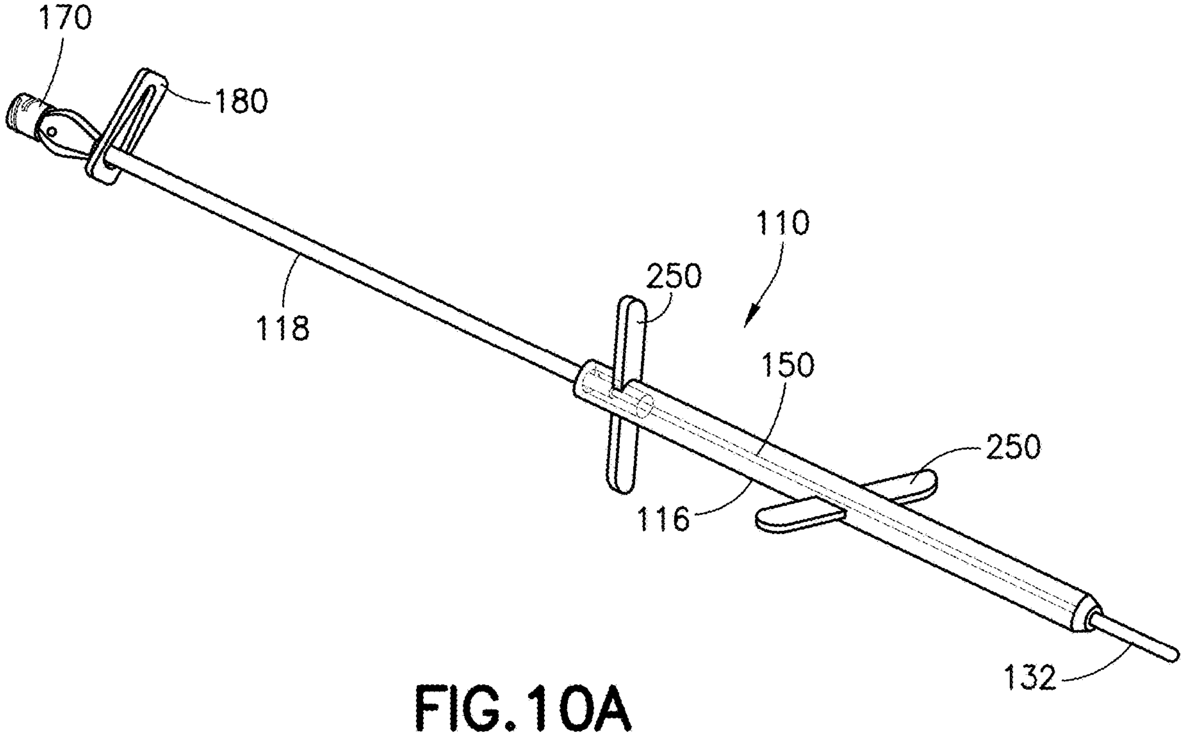
FIGS. 10A-10B are perspective views of a medical device according to non-limiting embodiments described herein.
Figure 10B:
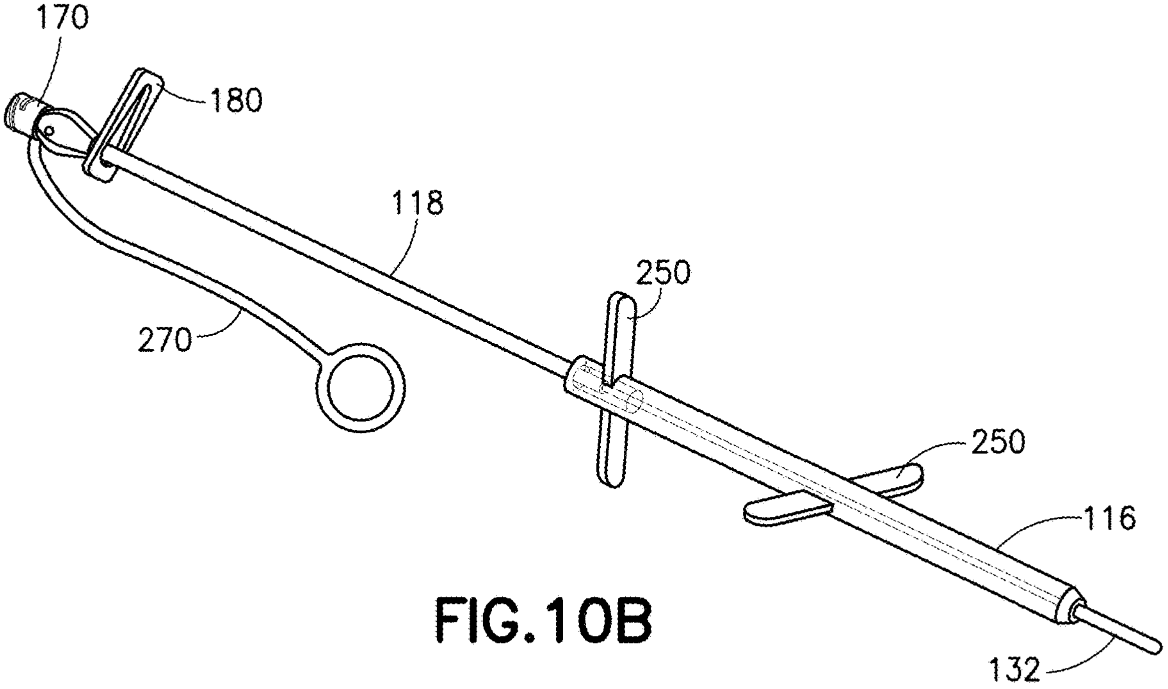
Figure 11A:
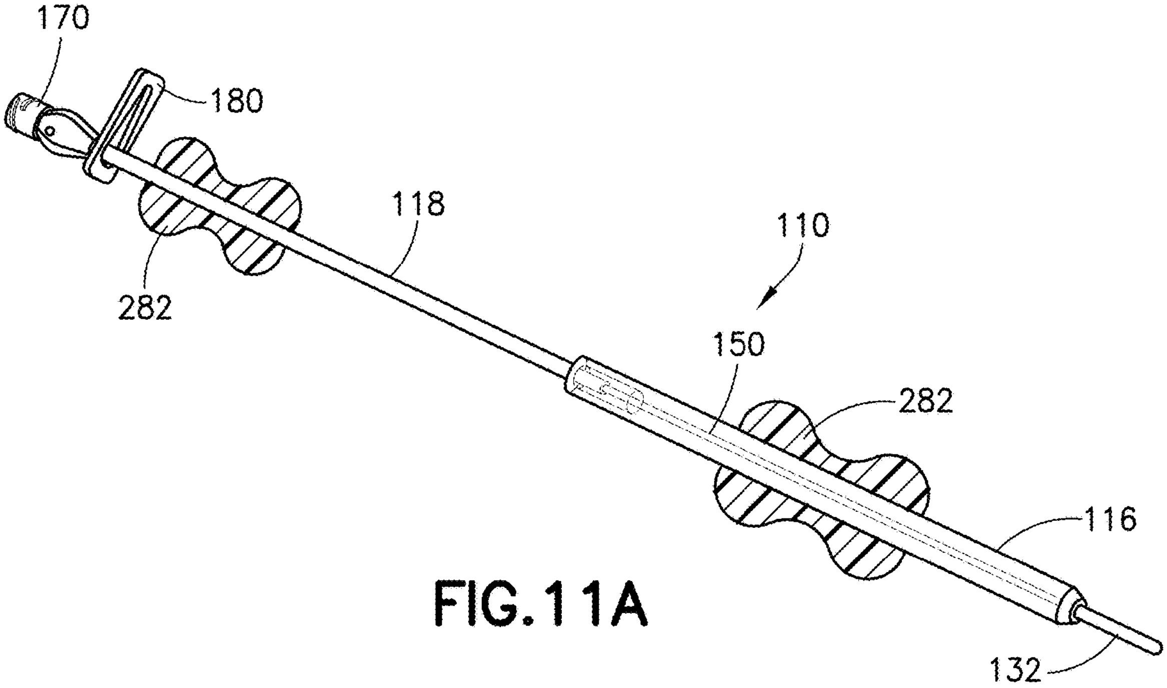
FIGS. 11A-11B are perspective views of a medical device according to non-limiting embodiments described herein.
Figure 11B:
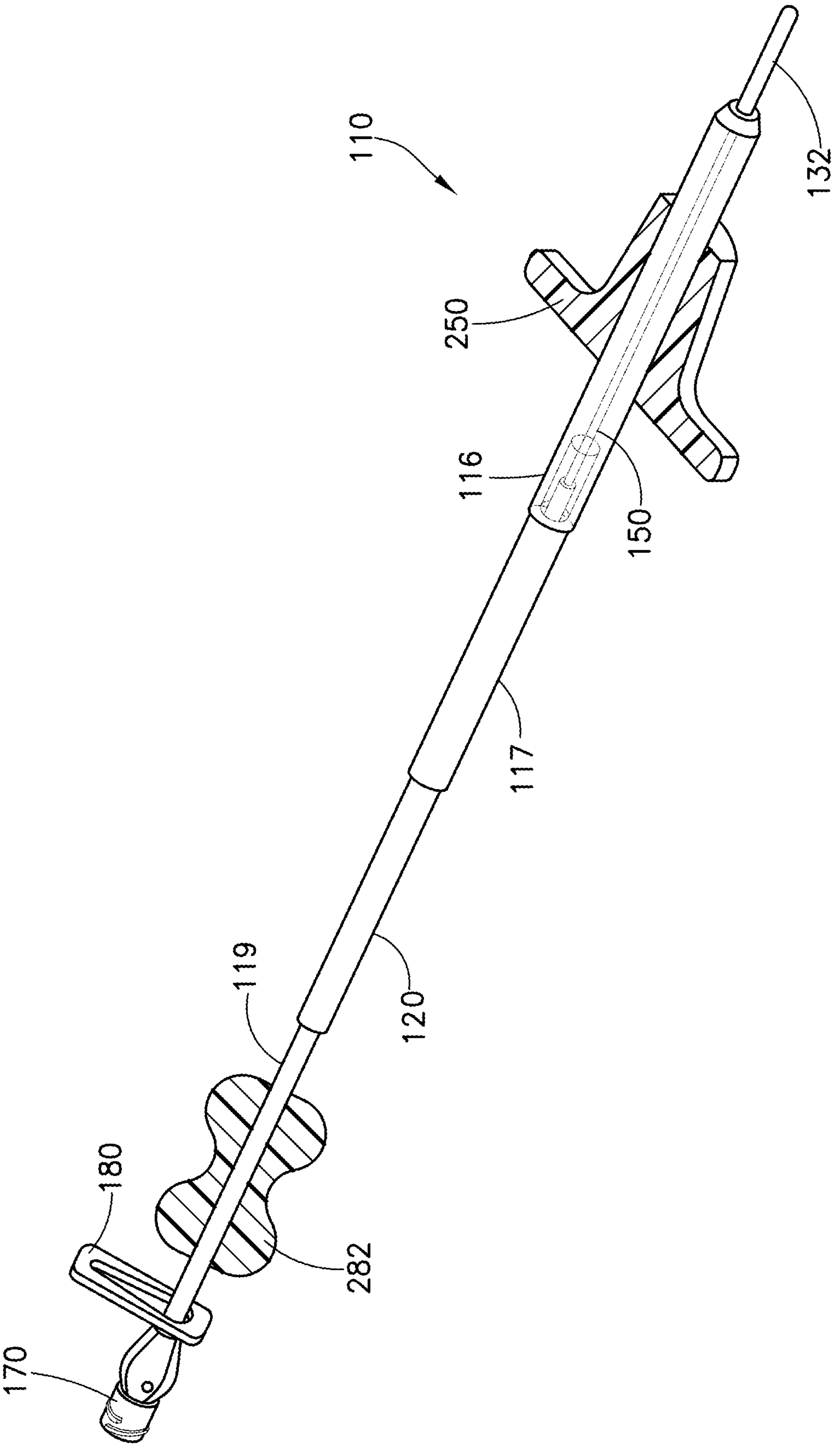
Figure 12:
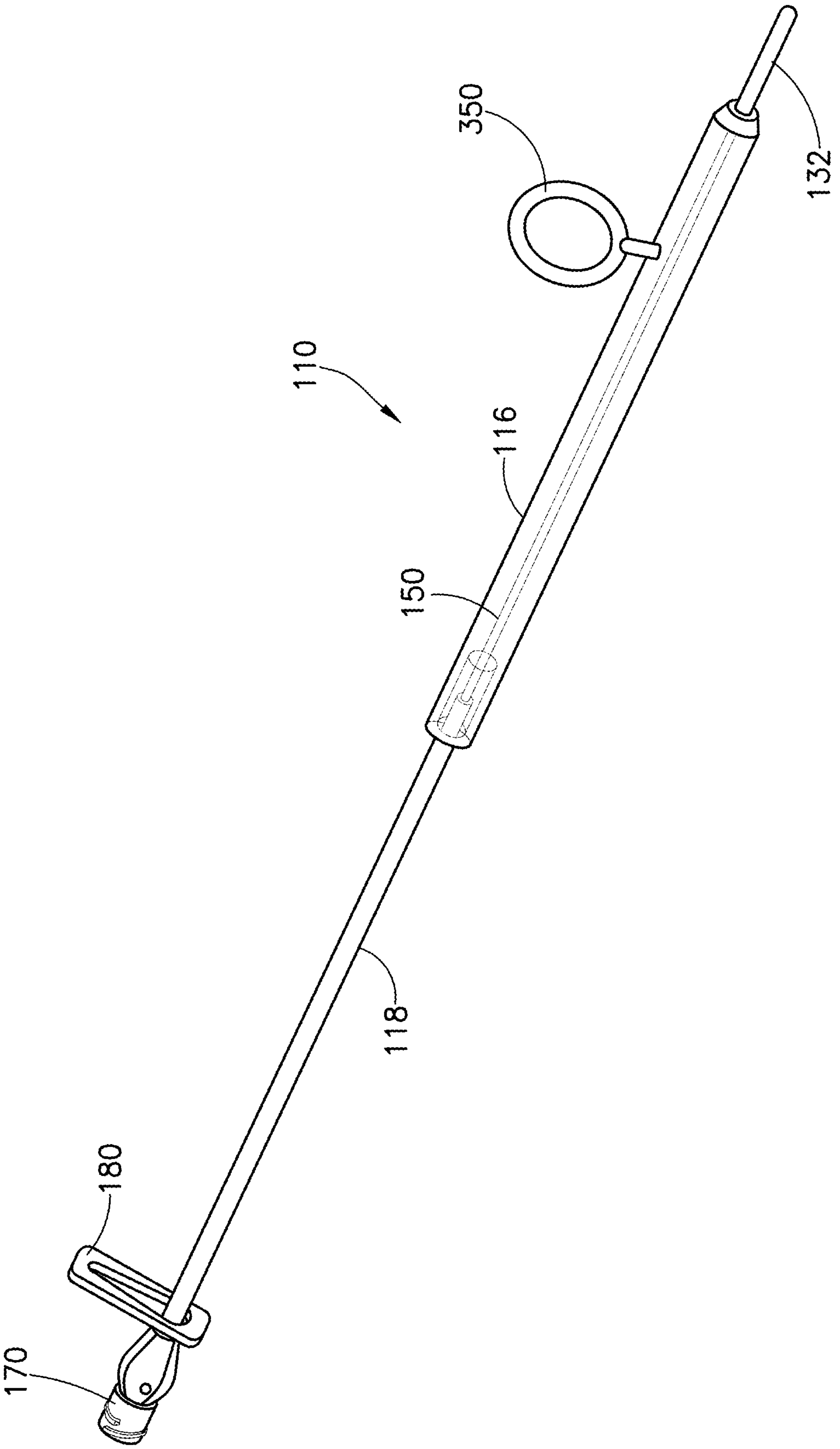
FIG. 12 is a perspective view of a medical device according to non-limiting embodiments described herein.

Turning to FIGS. 10-12, in non-limiting embodiments outer housing 116 and/or inner housing 118 may include one or more features to assist a user in securely and reliably gripping instrument delivery device 110 for accurate advancement and manipulation of an instrument. As shown in FIG. 10A, outer housing 116 may include one or more flanges 250, though those of skill will appreciate that the orientations may be adjusted, and that the illustrated orientation of FIG. 10A is merely one possibility. As shown in FIG. 10B, in non-limiting embodiments, outer housing 116 may include one or more flanges 250, and inner housing 118 may include a tether 270, to allow for a user to advance inner housing 118 and/or instrument in a similar manner to a syringe plunger (e.g., by placing forefinger and index finger on one or both of flanges 250 and, with a thumb, advancing inner housing 118 by placing thumb into a ring on tether 270 and applying a distally-directed force. As shown in FIG. 11A, in place of, or in addition to, flanges 250, one or more grips 282 may be supplied at any suitable location on outer housing 116 and/or inner housing 118. Suitable grips 282 may be formed of an ergonomic material, to provide comfort while a user grips the instrument delivery device 110, and may include features to, for example, increase grip and prevent slippage while inner housing 118 is being advanced/retracted.

With reference to the non-limiting embodiment of FIG. 11B, inner housing may include one or more grips 282 and a plurality of telescoping inner housing portions 117, 120, 119. In non-limiting embodiments, a process of advancing the instrument involves nesting a first inner housing portion 119 within a second housing portion 120, and nesting second housing portion 120 within third housing portion 117. In non-limiting embodiments, third housing portion 117 is slidably received within outer housing 116, such that inner housing may be slidably received entirely, or almost entirely, within outer housing 116. Each portion of inner housing includes a proximal end and a distal end and, in non-limiting embodiments, inner housing portions 117, 120, 119 may have a variable diameter, to allow for the telescoping relationship. Instrument delivery device 110 further includes an instrument, exemplified in the drawings as catheter or fluid conduit 150, but, as described previously and as will be appreciated by those of skill in the art, may be any medical instrument that can be delivered through catheter assembly 10 to a patient's vasculature. Fluid conduit 150 is slidably received within outer housing 116, and may be advanced and/or retracted relative to outer housing 116 by displacement of inner housing (e.g., telescoping housing portions 117, 120, 119) relative to outer housing 116. In non-limiting embodiments, various portions 117, 120, and/or 119 of inner housing may include a lubricant therebetween, and/or between an inner housing portion and outer housing 116, and/or between the instrument and the inner housing portions 117, 120, and/or 119 and/or outer housing 116, so as to reduce the force needed to advance the instrument (such as fluid conduit 150). As shown in FIG. 11B, grip 282 may be arranged on first telescoping portion 119, though those of skill will appreciate that other arrangements fall within the scope of the present disclosure.

Turning to FIG. 12, in non-limiting embodiments, outer housing 116 may include a ring 350, to provide a user with a location to grip outer housing 116 for advancement of inner housing 118 and/or instrument. Ring 350 may be formed of an ergonomic material, to provide comfort while a user grips the instrument delivery device 110, and may include features to, for example, increase grip and prevent slippage while inner housing 118 is being advanced/retracted.

Although the present disclosure has been described in detail for the purpose of illustration based on what is currently considered to be the most practical and preferred embodiments or aspects, it is to be understood that such detail is solely for that purpose and that the present disclosure is not limited to the disclosed embodiments or aspects, but, on the contrary, is intended to cover modifications and equivalent arrangements that are within the spirit and scope of the appended claims. For example, it is to be understood that the present disclosure contemplates that, to the extent possible, one or more features of any embodiment may be combined with one or more features of any other embodiment.

The invention claimed is:

1. A medical device, comprising:

an instrument having a proximal end and a distal end;

an introducer configured to moveably receive the instrument and having:

an outer housing having a proximal end, a distal end, and a sidewall therebetween defining an inner volume, the sidewall comprising a plurality of alternating first and second regions, the first regions having a first inner diameter and the second regions having a second inner diameter that is less than the first inner diameter; and an inner housing having a proximal end, a distal end, and a sidewall therebetween defining an inner volume and an outer diameter, wherein the outer diameter of the inner housing is substantially equal to the second inner diameter of the outer housing, the inner housing slidably received within the outer housing;

the distal end of the introducer configured to couple the introducer to an intravenous line; and wherein the inner housing is configured to move relative to the outer housing to move the instrument between a first position, in which the instrument is disposed within the outer housing, and a second position, in which the distal end of the instrument is disposed beyond the distal end of the outer housing such that at least a first portion of the instrument is disposed within the intravenous line when the introducer is coupled to the intravenous line.

2. The medical device of claim 1, wherein the outer housing comprises a lock at the distal end thereof, the lock configured to couple the introducer to the intravenous line.

3. The medical device of claim 2, wherein a joint is arranged at the distal end of the outer housing between the distal end of the outer housing and the lock.

4. The medical device of claim 1, wherein the outer housing is substantially transparent.

5. The medical device of claim 1, further comprising one or more indicia arranged on the inner housing and/or the instrument and corresponding to instrument length and/or instrument position relative to the intravenous line.

6. The medical device of claim 5, wherein the one or more indicia are visual and/or tactile indicia.

7. The medical device of claim 1, further comprising a stop arranged on the inner housing, the stop configured to prevent advancement of the inner housing into the outer housing.

8. The medical device of claim 7, wherein a position of the stop corresponds to a length of the instrument.

9. The medical device of claim 1, further comprising one or more indicia arranged on the outer housing and corresponding to instrument length and/or instrument position relative to the intravenous line.

10. The medical device of claim 1, wherein the inner housing and/or the outer housing comprise one or more flanges configured to be gripped by a user.

11. The medical device of claim 1, wherein the inner housing comprises a tether configured to be gripped by a user.

12. The medical device of claim 1, wherein the inner housing and/or the outer housing comprise one or more grips configured to be gripped by a user.

13. The medical device of claim 1, wherein the inner housing comprises one or more grips and the outer housing comprises one or more flanges, the one or more grips and the one or more flanges configured to be gripped by a user.

14. The medical device of claim 1, wherein the outer housing comprises a ring arranged on the sidewall thereof, the ring configured to be gripped by a user.

15. The medical device of claim 1, wherein the instrument is one or more of a catheter, guidewire, obturator, wire, electrical wiring, probe, light pipe, and sensor.

16. The medical device of claim 1, wherein the instrument is a catheter.

17. The medical device of claim 16, wherein the inner housing comprises a clamp at the proximal end thereof, configured to selectively block fluid flow through the inner housing.

18. The medical device of claim 17, wherein the inner housing is in fluid communication with the catheter, such that fluid flowing proximally from the catheter is received within the inner housing.

19. The medical device of claim 18, wherein the inner housing further comprises a fluid conduit in fluid communication with the catheter.

20. The medical device of claim 19, wherein the fluid conduit extends proximally beyond the proximal end of the inner housing.

21. The medical device of claim 18, further comprising a fluid conduit coupled to the proximal end of the inner housing.

22. The medical device of claim 1, wherein the inner housing is formed of a material with sufficient stiffness to limit and/or prevent buckling of the inner housing as the inner housing is advanced through the outer housing.

23. The medical device of claim 1, wherein the inner housing comprises a connector at the proximal end thereof.

24. A system, comprising:

a catheter assembly comprising:

a catheter adapter, comprising a distal end;

a proximal end;

a lumen extending between the distal end and the proximal end; and a side port arranged between the distal end and the proximal end, the side port in fluid communication with the lumen;

a catheter secured to the distal end of the catheter adapter and extending distally from the catheter adapter; and a fluid conduit having a distal end coupled to the side port and a proximal end, the fluid conduit in fluid communication with the side port; and the medical device of claim 1.

* * * * *